US00PP08448P

United States Patent [19]

Meilland

[11] Patent Number: Plant 8,448

[45] Date of Patent: Nov. 9, 1993

[54] MINIATURE ROSE PLANT—MEIBEKARB VARIETY

[75] Inventor: Alain A. Meilland, Antibes, France

[73] Assignee: The Conard-Pyle Company, West Grove, Pa.

[21] Appl. No.: 921,092

[22] Filed: Jul. 29, 1992

[51] Int. Cl.[5] ..... A01H 5/00
[52] U.S. Cl. ..... Plt./10
[58] Field of Search ..... Plt. 7.1, 10

*Primary Examiner*—Howard J. Locker
*Attorney, Agent, or Firm*—Burns, Doane, Swecker & Mathis

[57] ABSTRACT

A new and distinct variety of rose plant of the Miniature Class is provided which forms abundantly and continuously attractive long lasting semi-double blossoms. The blossoms initially are Cardinal Red and turn to Tyrian Purple when open and finally to Rose Bengal when fully open. The new variety originated as a spontaneous mutation of unknown causation of the Meibarke variety (U.S. Plant Pat. No. 6,791). The plant is bushy and forms vigorous vegetation. The plant is particularly suited for growing as ornamentation in the garden. Additionally, the plant tends to be less affected by crytogamic diseases than most other rose varieties of the Miniature Class.

1 Drawing Sheet

SUMMARY OF THE INVENTION

The new variety of Miniature rose plant was discovered in France while growing among plants of the Meibarke variety (U.S. Plant Pat. No. 6,791). It is believed to be a spontaneous mutation of unknown causation. The plant of the new variety has been carefully preserved and studied. Had I not discovered and preserved this new variety and subjected it to study it would have been lost to mankind.

The new can be ready distinguished from Meibarke variety upon an examination of the blossom coloration. More specifically, the Meibarke variety exhibits bicolored blossoms which are whitish in coloration and suffused at wide margins with Cardinal Red. The blossom coloration of the new variety of the present invention is as described in detail hereafter.

It was found that the new variety of Miniature rose plant of the present invention possesses the following combination of characteristics:

(a) forms abundantly and continuously attractive semi-double long lasting blossoms which initially are Cardinal Red and turn to Tyrian Purple when open and finally to Rose Bengal when fully open,
(b) forms vigorous vegetation,
(c) exhibits a bushy growth habit,
(d) is particularly well adapted for growing as ornamentation in the garden, and
(e) is less affected by crytogamic diseases than most other rose varieties of the Miniature class.

The new variety well meets the needs of the horticultural industry for all usages. It is particularly well-suited for use as attractive ornamentation for the garden.

The new variety has been found to undergo asexual propagation by a number of routes, including budding, grafting, cuttage, etc. Asexual propagation by the above-mentioned methods as performed in France and at West Grove, Pa., has shown that the above characteristics of the new variety are strictly transmissible from one generation to another.

The new variety has been named the Meibekarb variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety described herein were 18 months of age and were observed during May while growing in one-gallon containers of their own roots in greenhouses at West Grove, Pa., U.S.A.

At the far left are shown the under surfaces of leaves with five leaflets (top and middle), and three leaflets (bottom). Adjacent these are shown the upper surfaces of leaves with seven leaflets (top), five leaflets (middle), and three leaflets (bottom). To the right is shown a segment of a flowering stem. At the bottom left is shown a floral receptacle wherein the pistils are visible with the sepals and stamens having been removed, and to the right of this a floral receptacle wherein only the sepals have been removed. At the top in the middle are shown two young shoots. At the top (far right) are shown two floral buds as the sepals open. To the left of these are shown two floral budes at an earlier stage of development wherein the sepals are yet to open to any substantial degree. At the middle (far right) are shown two floral buds as the petals begin to open. Adjacent to these in the center is shown a flower in the course of opening. Adjacent to this is shown a pair of open flowers with the upper surface being illustrated on the right and the under surface on the left. At the bottom are shown two pairs of fully open flowers with the upper surfaces being illustrated on the right and the under surfaces on the left.

DETAILED DESCRIPTION

The chart used in the identification of the colors is that of The Royal Horticultural Society (R.H.S. Colour Chart). The terminology which precedes reference to the chart has been added to indicate the corresponding colors in common terms. The description is based on 18 month-old specimens of the new variety which were observed during May while growing in one-gallon containers on their own roots in greenhouses at West Grove, Pa., U.S.A.

Class: Miniature.

Plant:

*Height.*—Approximately 40 to 45 cm. on average.

*Habit.*—Bushy.

Branches:

*Color.*—Young stems: light green, Yellow-Green Group 146C and widely shaded with a reddish tint. Adult wood: medium green, Yellow-Green Group 146B.

*Thorns.*—As illustrated in the photograph.

Leaves:

*Petioles.*—Upper surface: grooved, reddish-brown on young foliage and medium green on adult foliage with glandular edges. Under surface: light green with some thorns.

*Stipules.*—Adnate, pectinate, very wide and linear.

*Leaflets.*—Number: 3, 5 (most often), and 7. Shape: oval with lance-shaped point. Serration: simple and regular. Texture: leathery. General appearance: dense and fairly-glossy. Color (young foliage): Upper surface: reddish-brown. Under surface: reddish-brown. Color (adult foliage): Upper surface: dark green, Yellow-Green Group 147A. Under surface: medium green, Yellow-Green Group 147B.

Inflorescence:

*Number of flowers.*—Approximately 1 to 9 per stem.

*Peduncle.*—Straight, medium green, rigid, and more or less shaded with reddish coloration, bears glandular aciculae, and its length is approximately 2 to 2.5 cm. on average.

*Sepals.*—Upper surface: tomentose and greenish in coloration with a reddish tint. Under surface: light green, more or less shaded with reddish coloration, with more or less glandular edges, and the outer sepals have edges which are more or less appendiculated.

*Buds.*—Shape: oval.

Length: approximately 1.5 cm. on average. Size: small. Color upon opening: Upper surface: Cardinal Red, Red Group 53A, near the edges of the petal turning to light Cardinal Red, Red Group 53C, towards the bottom of the petal, with a very wide ligth-yellowish base. Under surface: Cardinal Red, Red Group 53A, turning to light Cardinal Red at the bottom of the petals with a light yellowish claw.

*Flower.*—Form: flat cuplike, and semi-double. Diameter: approximately 4.5 cm. on average. Color (when opening begins): Upper surface: strong Cardinal Red, Red Group 53B, turning to Rose Bengal, Red-Purple Group 57B, at the middle of the petal and to light orange near the base of the petal. Under surface: Rose Bengal, Red-Purple Group 57B, turning to light Cardinal Red, Red Group 53D, with a wide light-yellowish claw. Color (when blooming): Upper surface: Tyrian Purple, Red-Purple Group 57A, turning to light Rose Bengal, Red-Purple Group 57C, at the middle of the petal and light orange near the base of the petal. Under surface: Rose Bengal, Red-Purple Group 57C, turning to Red-Purple Group 57D towards the base of the petal with a wide light yellowish claw. Color (at end of blooming): Upper surface: light Rose Bengal, Red-Purple Group 57B, turning to Red-Purple Group 57C at the middle of the petal and whitish near the base of the petals. Under surface: light Rose Bengal, Red-Purple Group 57C, turning to Red-Purple Group 57D and yellowish towards the center of the petals. Fragrance: none. Lasting quality: long. Petal number: approximately 20 on average. Petal form: generally rounded. Petal texture: firm. Petal drop: excellent, with petals dropping off very cleanly. Anthers: normal and bright yellow in coloration. Stamen number: approximately 93 to 98 on average. Filaments: yellowish and of irregular heights. Pistil number: approximately 35 to 37 on average. Stigmas: normal and straw-like in coloration. Styles: light green, fuchsia near the tip, and of irregular heights. Receptacle: light green, and at the dehiscence of the anthers in longitudinal section it is in the shape of a jug.

Development:

*Vegetation.*—Vigorous.

*Blooming.*—Abundant and continuous.

*Resistance to frost.*—Good.

*Resistance to diseases.*—Good.

pg,11

I claim:

1. A new and distinct variety of Miniature rose plant characterized by the following combination of characteristics:

(a) forms abundantly and continuously attractive semi-double long lasting blossoms which initially are Cardinal Red and turn to Tyrian Purple when open and finally to Rose Bengal when fully open, (b) forms vigorous vegetation, (c) exhibits a bushy growth habit, (d) is particularly well adapted for growing as ornamentation in the garden, and (e) is less affected by crytogamic diseases than most other rose varieties of the Miniature Class;

substantially as herein shown and described.

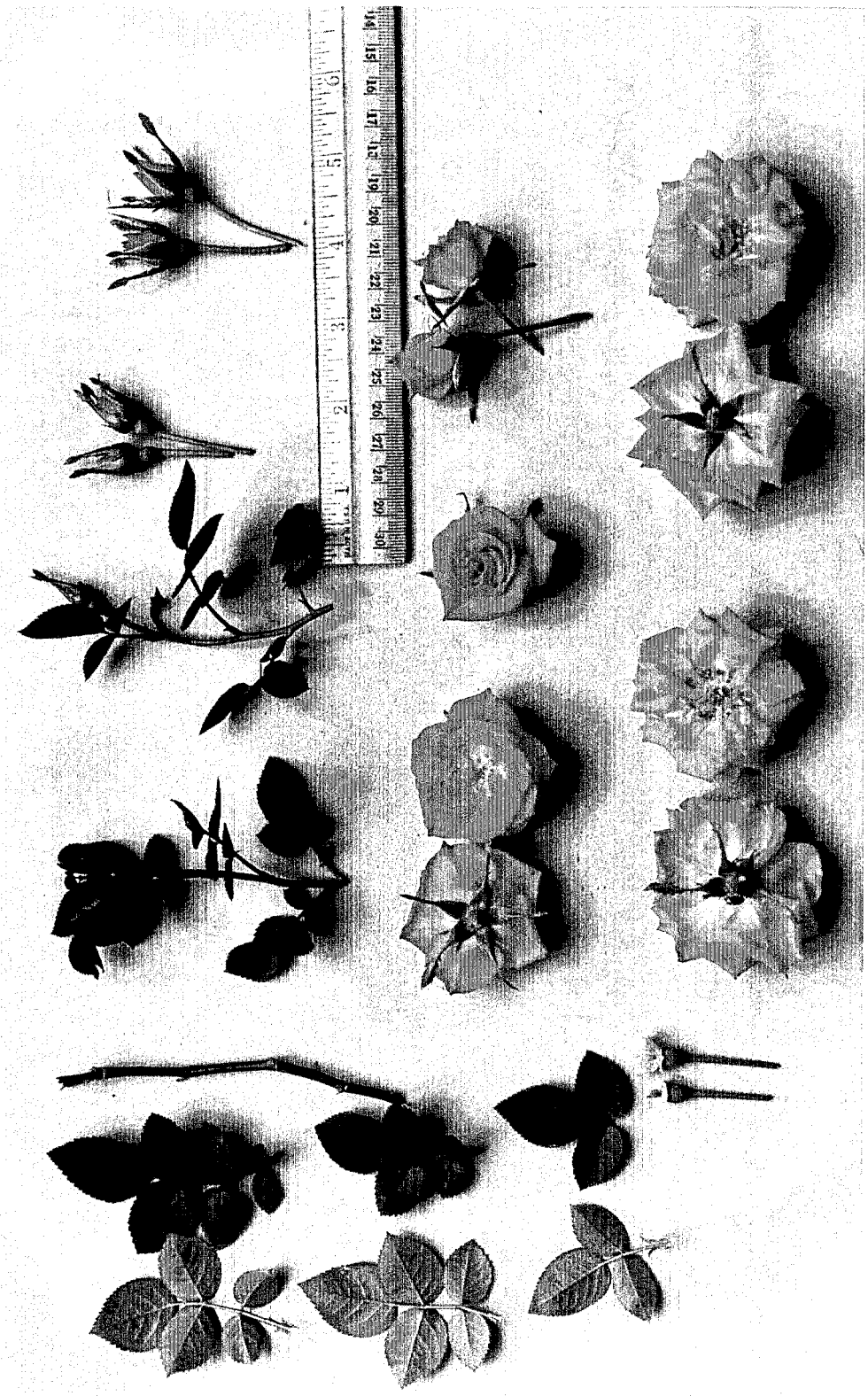

* * * * *